United States Patent [19]

Cascone

[11] Patent Number: 4,526,750
[45] Date of Patent: Jul. 2, 1985

[54] NON-STAINING PALLADIUM BASED DENTAL ALLOY

[75] Inventor: Paul J. Cascone, Yorktown Heights, N.Y.

[73] Assignee: Pennwalt Corporation, Philadelphia, Pa.

[21] Appl. No.: 571,305

[22] Filed: Jan. 16, 1984

[51] Int. Cl.³ .................................................. C22C 5/04
[52] U.S. Cl. ..................................... 420/463; 420/590
[58] Field of Search ................ 420/463, 464, 465, 590

[56] References Cited

U.S. PATENT DOCUMENTS

| | | | |
|---|---|---|---|
| 4,123,262 | 10/1978 | Cascone | 420/463 |
| 4,261,744 | 4/1981 | Boyajian | 420/463 |
| 4,319,877 | 3/1982 | Boyajian | 420/463 |
| 4,336,290 | 6/1982 | Tsai | 420/463 |
| 4,387,072 | 6/1983 | Schaffer | 420/463 |
| 4,400,350 | 8/1983 | Wagner | 420/464 |
| 4,412,970 | 11/1983 | Prasad | 420/463 |
| 4,419,325 | 12/1983 | Prasad | 420/464 |

Primary Examiner—Peter K. Skiff
Assistant Examiner—S. Kastler

[57] ABSTRACT

A thermally stable, non-staining, silver and gold free, palladium-based dental alloy for use with the porcelain fused-to-metal technique, said alloy containing specified minor amounts of cobalt, gallium and ruthenium, iridium or rhenium, and the method for preparing the alloy are disclosed herein.

3 Claims, No Drawings

NON-STAINING PALLADIUM BASED DENTAL ALLOY

FIELD OF THE INVENTION

This invention relates to a non-staining, palladium-based dental alloy used for the fabrication and repair of dental prostheses with the porcelain fused-to-metal technique. More particularly, the invention relates to a gold and silver free, palladium-based alloy containing minor proportions of cobalt, gallium and ruthenium (iridium or rhenium) such that the alloy is thermally stable within the temperature range (porcelain firing range) used in many dental laboratories and exhibits a sufficiently high solidus temperature enabling pre-soldering of the alloy without distortion of the restoration.

BACKGROUND OF THE INVENTION

The Prior Art

Silver and gold-free palladium-based dental alloys have previously been disclosed in the literature. However, these prior disclosures suffer from various deficiencies. U.S. Pat. No. 4,261,744, issued Apr. 14, 1981, covers a dental alloy composition of 5–10 weight % indium, 5–10.5 weight % tin, up to 7.5 weight % cobalt, chromium or nickel, up to 0.25 weight % silicon and a balance of palladium. The incorporation of silicon in this composition in the given quantity will produce a low melting eutectic phase of silicon and palladium. This phase melts at 800° C. which is lower than the porcelain firing temperature range of 960°–1010° C. Distortion of the restoration may occur during normal porcelain firing due to the lower melting temperature of the eutectic phase. In addition, the low melting temperature eutectic phase will hamper efforts to join restoration sections together by soldering prior to porcelain firing. This "pre-soldering" operation takes place at 1050°–1120° C. and the low melting temperature eutectic phase causes a portion of the alloy to be molten which may easily result in distortion of the prosthesis.

The composition of the above mentioned patent and similar compositions on the market do not contain a grain refiner e.g., ruthenium, iridium or rhenium to assure a single phase homogeneous material devoid of large grains. The presences of such large grains (about 400–600 microns) fosters the phenomena known as "hot tearing" and "marginal flaking". "Hot tearing" means the fracturing of the alloy casting during solidification in the investment. "Marginal flaking" occurs when stress is applied to the edges of the alloy casting and small pieces break off as a result.

U.S. Pat. No. 4,123,262 discloses a non-staining alloy intended for use in the porcelain fused-to-metal technique. However, the alloy composition of the patent requires the expensive gold component for successful results.

U.S. Pat. No. 4,387,072 issued June 7, 1983, discloses a dental alloy comprising by weight 50–85% of palladium, 5–40% copper and/or cobalt, 1–15% gallium, up to 5% of nickel, gold, indium, ruthenium or tin, up to 0.5% rhenium and/or iridium and up to 1% boron. The reference does not teach or suggest the combination and appropriate concentrations of metals to provide an alloy having all of the beneficial properties of the alloy of this invention and it does not disclose the necessity of the formation of the proper oxide for satisfactory adherence of the alloy to porcelain when preparing dental restorations. The alloy product sold under this patent, which contains by weight 79% palladium, 2% gold, 10% copper and 9% gallium, exhibits a eutectic phase and requires the user to heat the alloy in air at 1010° C. for five minutes or until a brown oxide is formed before applying the porcelain. In contrast, the alloys of the present invention are immediately ready for application of porcelain when reaching the porcelain firing temperature range. This results in a substantial savings of time in the preparation of dental restorations.

STATEMENT OF THE INVENTION

This invention is a single phase, gold and silver-free dental alloy comprising from about 3 to about 4.5 weight % cobalt, from about 8 to about 9 weight % gallium, from about 0.4 to about 1.0 weight % ruthenium, iridium or rhenium and a balance of palladium. This single melt phase alloy exhibits (i) a homogeneous structure devoid of a eutectic phase during exposure to a simulated porcelain firing cycle, (ii) a liquidous temperature below about 1300° C., (iii) a solidus temperature above about 1120° C., and (iv) a grain size of less than 200 microns.

In another aspect of this invention, the dental alloy is prepared by mixing in a crucible having walls of either magnesia, zirconia or high purity alumina, the following components in amounts based on the weight of the dental alloy:

(a) from 10 to 25% of a binary mixture of about 96 weight % palladium and about 4 weight % ruthenium, iridium or rhenium, (b) from 23 to 26% of a binary mixture of about 65 weight % palladium and about 35 weight % gallium, (c) from about 3 to about 4.5% cobalt and (d) a balance of palladium, and heating the components in said crucible in air to a temperature in the range of 1400° to 1440° C. until completely molten.

DETAILED DESCRIPTION OF THE INVENTION

The alloys of this invention are particularly useful for the porcelain fused-to-metal procedure employed in the fabrication of dental prostheses. They are similar in properties to those alloys described in U.S. Pat. No. 4,123,262 but are palladium-based compositions formulated to omit the costly gold ingredient while retaining excellent working characteristics. Their composition also omits silver which can cause staining or discoloration of the porcelain material bonded to the alloy casting. They are thermally stable owing to the fact that they exhibit no eutectic phase in which the solid solubility of the solute (components of lesser amounts) in the solvent (metal base of alloy) is exceeded.

The alloys of this invention have a liquidus temperature (temperature above which all alloy components are liquid) below about 1300° C. so that they can be cast at a temperature within the range of heating of a gas/oxygen torch, the primary heating means used for casting in dental laboratories. The solidus temperature (temperature below which all alloy components are solid) of the alloys is above about 1120° C., enabling pre-soldering and porcelain firing with castings of the alloys without distortion, caused by sagging occuring in the restoration.

The alloys exhibit single phase, homogeneous microstructures after simulated porcelain firing at 1900° F. and are devoid of a eutectic phases. The firing simulation involves heating in air an alloy sample weighing 5 gms. by bringing the heating furnace temperature to 1900° F. (1037° C.) at a rate of increase ranging from 75° (23.85° C.) to 100° F. (37.5° C.) per minute, holding at 1900° F. for about 10 minutes, removing the alloy sample from the furnace and allowing it to cool to room temperature under a refractory cover without external cooling means.

The components and their ranges of concentration used in the alloy of the invention are as follows:
Cobalt—3.0 to 4.5 (preferable 4.0) weight %
Gallium—8.0 to 9.0 (preferably 8.5) weight %
Ruthenium, iridium or rhenium—0.4 to 1.0 (preferably 0.8) weight %
Palladium balance to 100%

Palladium is, of course, used because of its relative low cost, workability, resistance to oxidation, good fusion characteristics and silver color.

Cobalt and gallium are included to lower the melting range of the alloy. Cobalt contents less than 3 weight % and/or gallium contents less than 7 weight % result in alloys having a liquidus temperature above 1300° C. which is above that temperature required for the gas-/oxygen torch casting used in many laboratories. Cobalt contents above 4.5 weight % may produce an alloy having undesirable ferro-magnetic properties. Gallium contents above 9.0 weight % produce a low melting eutectic phase in the alloy and a solidus temperature below 1120° C. which, as previously stated, can cause distortion when pre-soldering or porcelain firing. The solidus temperature of an alloy of the composition described herein can be estimated by use of the following equation:

$$\text{Solidus Temp. °C.} = 1496 - 11 \text{ (wt. \% Cobalt } - 36 \text{ (wt. \% gallium)}$$

Ruthenium (less preferably, iridium or rhenium) is essential to the alloy composition to provide an alloy having a grain size below about 200 microns thereby avoiding the "hot tearing" and "marginal flaking", phenomena which have been previously explained.

The "grain size" of an alloy as used herein means the average diameter of the grain in the alloy composition under examination.

The method of this invention is advantageously used in preparing the alloys described herein because gallium alone has a melt temperature which is too low and ruthenium alone has a melt temperature which is too high for the processing temperature range used to prepare the alloy. The binary mixtures of palladium/gallium and palladium/ruthenium, identified above, have melt temperatures which are completely within the processing temperature range required to prepare the alloys.

EXAMPLE

In the following example, set forth to demonstrate the alloys and method of this invention, the alloys are prepared and cast in the following manner:

A high purity, alumina crucible is set in a tilt-pour electric induction furnace along with an ingot or restoration casting mold with means for preheating the mold. The mold is clamped below the crucible for receiving molten alloy when poured from the tilted crucible. The alloy components are introduced to the crucible in the following order:

(a) one-half the required quantity of palladium for the alloy composition.

(b) the total quantity of required gallium (8–9 wt. %) furnished in a binary mixture of about 65 weight % palladium and about 35 weight % gallium, (c) the total quantity of required cobalt (3–4.5 wt. %), and (d) the total quantity of required ruthenium (0.4–1.0 wt. %) furnished in a binary mixture of about 96 weight % palladium and about 4 weight % ruthenium.

The induction furnace is turned on to heat the crucible (about 1425° C.) until all components are completely melted and the melt is mechanically stirred for about 30 seconds. The remaining required palladium is added to the crucible and allowed to melt completely with stirring of the melt. At this time, if scraps of the same alloy composition are to be added to the melt, small increments are introduced allowing the additions to melt completely. The melt is brought to a temperature of 1425° C. with stirring and then the crucible is tilted somewhat to heat its pouring limps. Keeping the melt temperature at least to 1425° C. but not exceeding 1438° C., the melt is quickly poured into the mold preheated to 65.5° C. After solidification, the ingot or casting is removed from the mold and quenched in water (room temperature).

The following table provides data of alloy samples, prepared in the above described manner, either meeting the composition of this invention and exhibiting satisfactory properties or failing to meet the concentration requirements of the composition and providing unsatisfactory properties.

TABLE

| Metal Component | Sample Number (wt. % of Component in Alloy*) | | | |
| --- | --- | --- | --- | --- |
| | 1 | 2 | 3 | 4 |
| Palladium | 86.9 | 89.3 | 87.3 | 85.3 |
| Gallium | 8.5 | 7.5 | 8.5 | 9.5 |
| Cobalt | 4.0 | 2.5 | 3.5 | 4.5 |
| Ruthenium | 0.7 | 0.6 | 0.7 | 0.7 |
| Solidus, °C. | 1145 | 1212 | 1144 | 1107 |
| Liquidus, °C. | 1289 | 1343 | 1295 | 1251 |

*Component percentage amounts rounded off to nearest tenth.

Samples 1 and 3 above satisfactorily meet the objectives of this invention in that they are single phase alloys having solidus temperatures above about 1120° C. and liquidus temperatures below about 1300° C. The alloys of these samples can be cast at a temperature within the heating range of a gas/oxygen torch and can be pre-soldered (prior to porcelain firing) to join restoration casting sections together without distorting the casting. Porcelain can be fused to castings of these alloys at porcelain firing temperatures without distortion of the prostheses.

Sample 2 contains less gallium than is required by the alloys of this invention and has a liquidus temperature which is too high to permit satisfactory casting by the gas/oxygen torch method. Sample 4 has a solidus temperature which is too low caused by an excess of gallium over that required for this invention. This sample will exhibit a eutectic phase at presoldering temperatures causing a portion of the alloy to be molten while the remaining portion is solid so that distortion of the prosthesis may easily result.

I claim:

1. A single phase, gold and silver-free dental alloy consisting of about 4.0 weight % cobalt, about 8.5 weight % gallium, about 0.8 weight % ruthenium, iridium or rhenium and a balance of palladium.

2. A method of preparing a single phase dental alloy comprising mixing in a crucible having walls of magnesia, zirconia or high purity alumina the following components in amounts based on the weight of said dental alloy:

(a) from 10 to 25% of a binary mixture of about 96 weight % palladium and about 4 weight % ruthenium, iridium or rhenium, (b) from 23 to 26% of a binary mixture of about 65 weight of palladium and about 35 weight % gallium, (c) from about 3 to about 4.5% cobalt and (d) a balance of palladium, and heating said components in said crucible in air to a temperature in the range of 1400° to 1440° C. until completely molten.

3. The method of claim 2 wherein component (a) is about 14–16% of a binary mixture of about 96 weight % palladium and about 4 weight % of ruthenium, (b) is about 24–25% and (c) is about 3.5 to 4%.

* * * * *